(12) United States Patent
Kaufman et al.

(10) Patent No.: US 8,772,348 B2
(45) Date of Patent: Jul. 8, 2014

(54) MATERIALS AND METHODS FOR PEST CONTROL

(75) Inventors: Phillip Edward Kaufman, Alachua, FL (US); Rajinder Singh Mann, Winter Haven, FL (US); Jerry Frank Butler, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 13/505,681

(22) PCT Filed: Dec. 3, 2010

(86) PCT No.: PCT/US2010/058894
§ 371 (c)(1), (2), (4) Date: May 2, 2012

(87) PCT Pub. No.: WO2011/069068
PCT Pub. Date: Jun. 9, 2011

(65) Prior Publication Data
US 2012/0232160 A1 Sep. 13, 2012

Related U.S. Application Data

(60) Provisional application No. 61/266,318, filed on Dec. 3, 2009.

(51) Int. Cl.
*A61K 31/122* (2006.01)
*A01N 35/02* (2006.01)

(52) U.S. Cl.
CPC ...................................... *A01N 35/02* (2013.01)
USPC ........................................................ 514/690

(58) Field of Classification Search
None
See application file for complete search history.

(56) References Cited

U.S. PATENT DOCUMENTS

| 5,091,423 | A | 2/1992 | Wilson et al. | |
|---|---|---|---|---|
| 5,354,783 | A | 10/1994 | Marin et al. | |
| 7,867,479 | B2 * | 1/2011 | Dunham et al. | 424/84 |
| 1991/5006562 | * | 4/1991 | Steltenkamp | 514/625 |
| 2005/0233938 | A1 * | 10/2005 | Delplancke et al. | 510/507 |
| 2011/0166192 | A1 * | 7/2011 | Lodha et al. | 514/372 |

FOREIGN PATENT DOCUMENTS

| FR | EP 1 042 953 A2 * | 11/2000 | A01N 31/04 |
|---|---|---|---|
| WO | WO 00/05964 A1 | 2/2000 | |

OTHER PUBLICATIONS

Kaufman, P.E. et al. "Evaluation of Semiochemical Toxicity to *Aedes aegypti, Ae. albopictus* and *Anopheles quadrimaculatus* (Diptera: Culicidae" *Pest Manag Sci*, Feb. 2010, vol. 66, pp. 497-504.

Kaufman, P.E. et al. "Insecticidal Potency of Novel Compounds on Multiple Insect Species of Medical and Veterinary Importance" *Pest Manag Sci*, Sep. 2010, vol. 67, pp. 26-35.

Yang, P. et al. "Adulticidal Activity of Five Essential Oils Against *Culex pipiens quinquefasciatus*" *J. Pestic. Sci*, 2005, vol. 30, No. 2, pp. 84-89.

* cited by examiner

*Primary Examiner* — San-Ming Hui
*Assistant Examiner* — Jeanmarie Calvillo
(74) *Attorney, Agent, or Firm* — Saliwanchik, Lloyd & Eisenschenk

(57) ABSTRACT

The present invention provides a novel insecticide formulation that not only demonstrates strong insecticidal and residual activity against a variety of insects, but also exhibits low mammalian toxicity. In certain embodiments, the present invention relates to the use of pesticidal compounds selected from beta damascone, CYCLEMONE A™, melafleur, and derivatives thereof for killing arthropod pests including, but not limited to, mosquitoes and flies. Specifically exemplified herein is the use of the compounds of the present invention to control three mosquitoes (*Aedes aegypti, Ae. albopictus,* and *Anopheles quadrimaculatus*), the house fly (*Musca domestica*), the stable fly (*Stomoxys calcitrans*) and the sand fly (*Lutzomyia shannoni*).

20 Claims, No Drawings

MATERIALS AND METHODS FOR PEST CONTROL

CROSS-REFERENCE TO A RELATED APPLICATION

This application is a National Stage Application of International Application Number PCT/US2010/058894, filed Dec. 3, 2010; which claims the benefit of U.S. Provisional Application No. 61/266,318, filed Dec. 3, 2009, both of which are incorporated herein by reference in their entirety.

GOVERNMENT SUPPORT

This invention was made with government support under Grant No. W9113M-06-S-0001 awarded by the FY2006 Deployed War Fighter Protection Research Program of the Armed Forces Pest Management Board (AFPMB) of the Department of Defense. The government has certain rights in the invention.

BACKGROUND OF THE INVENTION

Insects and other arthropod pests are vectors of numerous parasitic and viral diseases, including for example malaria, dengue, yellow fever, chikungunya and encephalitis. In addition, these pests destroy foliage and fruits and cause harm to livestock. Among these pests, mosquitoes, filth flies, sand flies and stable flies are especially notorious for their negative impacts on the quality of human life. It has been estimated that mosquitoes transmit diseases to more than 700 million people annually worldwide. In addition, damages to livestock caused by the stable fly, *Stomoxys calcitrans* (L.), and house fly, *Musca domestica* (L.) alone exceed $1 billion annually.

Conventional synthetic insecticides such as chlorinated phenyl and cyclodiene compounds are noted for the strong mode of action on a variety of arthropod pests; however, their high toxicity also presents significant risks to human health and the environment.

At present, pyrethroids such as permethrin are the only class of synthetic insecticides recommended by the World Health Organization (WHO) for mosquitoes. Pyrethroids exhibit lower toxicity for mammals and moderate residual effects; thus, they have been widely used in a multitude of settings. The widespread use of pyrethroids, however, presents a new obstacle: it drives the selective adaptation of the pest species, resulting in pests with increased resistance and decreased susceptibility.

In light of the above described problems, there is a pressing need for the development of novel insecticides that are not only capable of controlling the target insects, but also exhibit low toxicity to humans and the environment. As will be clear from the disclosure that follows, these and other benefits are provided by the present invention.

BRIEF SUMMARY OF THE INVENTION

The present invention provides pesticidal compounds selected from beta damascone, CYCLEMONE A™, melafleur, and derivatives thereof. Advantageously, the compounds of the present invention not only demonstrate strong pesticidal and residual activity against a variety of arthropod pests, at low dosages, but also have low toxicity to mammals.

A further aspect of the present invention provides formulations comprising one or more pesticidal compounds selected from beta damascone, CYCLEMONE A™, melafleur, and derivatives thereof. The pesticidal formulations of the present invention can be, for example, emulsifiable concentrates.

The pesticidal formulations can be applied on materials such as, for example, paper, wood boards, leather, adhesives, paint, fabrics, and synthetic materials. In one embodiment, the pesticidal formulations can be applied on camouflage military fabrics.

The pesticidal formulations of the present invention can be used to control a variety of arthropod pests including, but not limited to, mosquitoes and other flies. Specifically exemplified herein is the use of the compounds of the present invention to control three mosquitoes (*Aedes aegypti, Ae. albopictus,* and *Anopheles quadrimaculatus*), the house fly (*Musca domestica*), the stable fly (*Stomoxys calcitrans*) and a sand fly (*Lutzomyia shannoni*).

In addition, the present invention provides methods for controlling insects. In one embodiment, the method comprises contacting an insect with an insecticidally effective amount of a compound or composition of the present invention.

DETAILED DISCLOSURE OF THE INVENTION

The present invention provides pesticidal compounds selected from beta damascone, CYCLEMONE A™, melafleur, and their derivatives. The present invention further provides pesticidal formulations comprising the compounds disclosed herein.

In addition, the present invention provides methods for controlling insects. In one embodiment, the method comprises contacting an insect with an insecticidally effective amount of a compound or composition of the present invention.

Compared to previously known chemicals having pesticidal activity such as, for example, semiochemicals, essential oils, or botanicals, the formulations of the present invention exhibit stronger toxicity against a variety of arthropod pests. Specifically, beta damascone, CYCLEMONE A™ and melafleur demonstrate stronger pesticidal activity against insects such as, for example, *Musca domestica, Aedes aegypti*, and *Stomoxys calcitrans*, compared to previously known semiochemical insecticides such as geranyl acetone, rosalva or citronellol. Insects exposed to these compounds exhibit impaired coordination, altered movements, tremors, paralysis and death, indicating that the formulations of the present invention are neurotoxic to these pests.

Advantageously, beta damascone, CYCLEMONE A™ and melafleur exhibit significant toxicity against insects that are resistant to conventional insecticides such as pyrethroids. It has been reported that insects such as the house fly, *Musca domestica*, are highly resistant to permethrin, beta cyfluthrin, and imidacloprid. In certain embodiments, the insecticidal formulations of the present invention, demonstrate activity against house flies that are known to be resistant to permethrin.

Further, as the formulation kills pests mainly through absorption via cuticular contact, the chemical breakdown of the active ingredient before absorption would result in a significant decline in pesticidal action. Studies have shown that conventional insecticides such as permethrin can be metabolically broken down in certain resistant insect strains, such as through the activation of esterases. As a result, these insects may be knocked down by permethrin in the beginning, but they are able to recover a few hours later.

Advantageously, beta damascone, CYCLEMONE A™ and melafleur exhibit little decline in toxicity against insect species such as house fly, *Musca domestica*, and yellow fever mosquito, *Aedes aegypti*, after a 24-hour holding period. In comparison, permethrin toxicity declines several folds against these pests after 24 hours, probably due to the breakdown of permethrin.

Despite their strong pesticidal action, the formulations of the present invention present little toxicity to humans and the environment. For instance, beta damascone and its derivatives belong to a family of closely related compounds known as rose ketones, and are widely used in perfumery, whisky and tobacco products. Also, CYCLEMONE A™, melafleur and their derivatives have a fresh fruity odor, and are widely used in the fragrance industry.

Additional target arthropod pests include, but are not limited to mites, ticks, and spiders. Further, beneficial insects such as honey bees are not impacted by the pesticidal formulations of the present invention.

DEFINITIONS

"Insecticide" or "pesticide" refers to a compound that has a lethal effect on insects or pests.

"Lethal concentration 50 ($LC_{50}$)" refers to a concentration of a pesticide for which essentially 50% of the target pests in contact with the pesticide are killed.

Similarly, "lethal concentration X ($LC_X$)" refers to a concentration of a pesticide for which essentially X % of the pests in contact with the pesticide are killed. For example, "Lethal concentration 90 ($LC_{90}$)" refers to a concentration of a pesticide for which essentially 90% of the target pests in contact with the pesticide are killed. "Lethal concentration 99 ($LC_{99}$)" refers to a concentration for which essentially 99% of the target pests are killed.

Pesticidal Compounds

In a first aspect, the present invention provides compounds having pesticidal activity.

In one embodiment, the compound has the following structure (Structure 1):

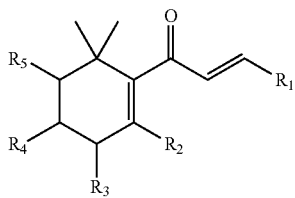

wherein $R_1$-$R_5$ are, independently, —H or alkyl such as, for example, $CH_3$, $C_2H_5$ or $C_3H_7$.

In another embodiment, the compound has the following structure (Structure 2):

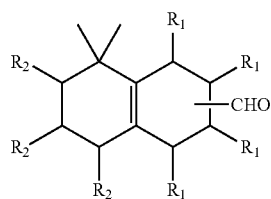

wherein $R_1$-$R_2$ are, independently, —H or alkyl such as, for example, $CH_3$, $C_2H_5$ or $C_3H_7$.

"Alkyl" means linear saturated monovalent radicals of one to eight carbon atoms or a branched saturated monovalent of three to eight carbon atoms. It may include hydrocarbon radicals of one to four or one to three carbon atoms, which may be linear. Examples include methyl, ethyl, propyl, 2-propyl, n-butyl, iso-butyl, tert-butyl, pentyl, and the like.

The present invention further pertains to isolated enantiomeric compounds. The isolated enantiomeric forms of the compounds of the invention are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the isolated enantiomeric compounds are at least about in 80%, 90%, 95%, or 99% enantiomeric excess.

In a specific embodiment, the pesticidal compound is beta damascone. Its structure is shown as follows:

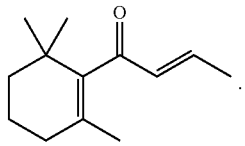

In one embodiment, the pesticidal agent is CYCLEMONE A™ (2-naphthaldehyde, 1,2,3,4,5,6,7,8-octahydro-8,8-dimethyl), and its structure is shown as follows:

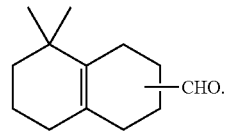

In a specific embodiment, the insecticidal compound can be melafleur (5,5-dimethyl-octahydro-2-naphthalene-carboxaldehyde). Melafleur has the following structure:

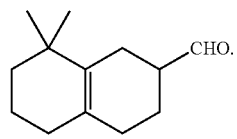

Pesticidal Formulations

In addition to pesticidal compounds, the present invention also provides pesticidal formulations. In one specific embodiment, the formulation comprises one or more active ingredients selected from beta damascone, CYCLEMONE A™, and melafleur. In one embodiment, the pesticidal formulation is in a form of an emulsifiable concentrate.

In one embodiment, the present invention provides pesticidal formulations comprising substantially pure pesticidal compounds. In preferred embodiments, the compounds of the present invention are at least 75% pure, preferably at least 90% pure, more preferably more than 95% pure, and most preferably more than 99% pure (substantially pure). The ready-to-use compositions of the present invention can comprise, for example, at least about 0.1%, 0.5%, 1.0%, 1.5%, 2.0%, 2.5%, 5.0%, 7.5% (w/w) or more of the active ingredient of the present invention (e.g. beta damascone, CYCEMONE A™, and/or melafleur). Typically, the concentration of the ready-to-use formulation will be 10% or less.

In one embodiment, the composition comprises a pesticidal compound of the present invention (e.g. beta damascone, CYCEMONE A™, and/or melafleur) at a concentration of about 5 µg cm$^{-2}$ to 200 µg cm$^{-2}$, 10 µg cm$^{-2}$ to 170 µg cm$^{-2}$, 10 µg cm$^{-2}$ to 150 µg cm$^{-2}$, 10 µg cm$^{-2}$ to 100 µg cm$^{-2}$, 10 µg cm$^{-2}$ to 90 µg cm$^{-2}$, 10 µg cm$^{-2}$ to 80 µg cm$^{-2}$, 10 µg cm$^{-2}$ to 70 µg cm$^{-2}$, 15 µg cm$^{-2}$ to 90 µg cm$^{-2}$, 15 µg cm$^{-2}$ to 80 µg cm$^{-2}$, 15 µg cm$^{-2}$ to 70 µg cm$^{-2}$, 20 µg cm$^{-2}$ to 70 µg cm$^{-2}$, 20 µg cm$^{-2}$ to 60 µg cm$^{-2}$, 20 µg cm$^{-2}$ to 50 µg cm$^{-2}$, 30 µg cm$^{-2}$ to 60 µg cm$^{-2}$, 30 µg cm$^{-2}$ to 50 µg cm$^{-2}$, or 40 µg cm$^{-2}$ to 60 µg cm$^{-2}$.

In one embodiment, the present invention provides a concentrated pesticidal formulation. The concentrated formulation may comprise, for example, at least about 25%, 50%, 70%, 90%, 95%, or 97% (w/w) of the active ingredient of the present invention. The concentrate can then be diluted with, preferably, an aqueous solution, to arrive at a ready-to-use formulation having a concentration of active ingredient as set forth above.

The formulation of the present invention can be produced in any manner known in the art, including, for example, chemical compounds in pure technical grade, aqueous solutions, aqueous concentrates, solid concentrates, powders, emulsions, emulsified concentrates, suspensions, dusts, pastes, granules, sprays, natural or synthetic materials or impregnated/encapsulated on materials.

The formulations of the present invention can optionally comprise suitable solvents, carriers, diluents, surfactants, antifoaming agents, extenders and/or emulsifiers, as is known in the art. Exemplary solvents and carriers include, but are not limited to, water; aromatics such as xylene, toluene or alkylnaphthalenes; aliphatic hydrocarbons such as cyclohexane or paraffins; mineral and vegetable oils; alcohols, such as butanol, ethanol, methanol, proponal, hexanol, heptanol, octanol, nonanol, decanol, diacetone alcohol, 2-ethoxyethanol or glycol and ethers and esters thereof; ketones such as acetone, methyl ethyl ketone, methyl isobutyl ketone or cyclohexanone; strongly polar solvents such as dimethylformamide and dimethyl sulphoxide; and waterketones, if appropriate.

In one specific embodiment, suitable solvents include oils such as for example aldehyde C16 (pure), alpha-terpineol, amyl cinnamic aldehyde, amyl salicylate, anisic aldehyde, benzyl alcohol, benzyl acetate, cinnamaldehyde, cinnamic alcohol, carvacrol, carveol, citral, citronellal, dimethyl salicylate, eucalyptol (cineole), eugenol, iso-eugenol, galaxolide, geraniol, guaiacol, ionone, menthol, methyl anthranilate, or 2-phenyl ethyl propionate, piperonal, piperonyl acetate, piperonyl alcohol, D-pulegone, terpinen-4-ol, terpinyl acetate, 4-tert butylcyclohexyl acetate, thyme oil, thymol, trans-anethole, vanillin and ethyl vanillin.

Exemplary emulsifiers and foam formers include, for example, nonionic and anionic emulsifiers, such as polyoxyethylene fatty acid esters, polyoxyethylene fatty alcohol ethers such as alkylaryl polyglycol ethers, alkylsulphonates, alkyl sulphates, and arylsulphonates.

In addition, the formulation of the present invention may further comprise optional active ingredients. Exemplary optional active ingredients include, but are not limited to, pyrethroids, geranyl acetone, rosalva, citronellol, essential oils such as aldehyde C16 (pure), alpha-terpineol, amyl cinnamic aldehyde, amyl salicylate, anisic aldehyde, benzyl alcohol, benzyl acetate, cinnamaldehyde, cinnamic alcohol, carvacrol, carveol, citral, citronellal, dimethyl salicylate, eucalyptol (cineole), eugenol, iso-eugenol, galaxolide, geraniol, guaiacol, ionone, menthol, methyl anthranilate, or 2-phenyl ethyl propionate, piperonal, piperonyl acetate, piperonyl alcohol, D-pulegone, terpinen-4-ol, terpinyl acetate, 4-tert butylcyclohexyl acetate, thyme oil, thymol, trans-anethole, vanillin, and ethyl vanillin.

The present invention also provides for the modification of the formulation such that the formulation is more chemically stable in storage and administration, i.e., once administered it has a longer time period of effectiveness as compared to the unmodified formulation.

Target Pests

Advantageously, it has been found that damascones, CYCLEMONE™s and melafleur exhibit potent pesticidal action against a variety of target pests, including arthropods.

In a specific embodiment, the formulation of the present invention is active on mosquito species, such as, for example, *Aedes aegypti, Aedes albopictus, Anopheles quadrimaculatus, Anopheles earlei, Anopheles punctipennis, Anopheles walkeri, Culex pipiens, Culex quinquefasciatus, Culex restuans, Culex salinarius, Aedes cinereus, Aedes vexans, Ochlerotatus japonicus, Ochlerotatus abserratus, Ochlerotatus atropalpus, Ochleortatus decticus, Ochlerotatus implicatus, Ochlerotatus intrudens, Ochlerotatus sollicitans,* and *Ochleortatus excrucians.*

In another specific embodiment, the formulation of the present invention is active on other fly species, such as, for example, *Musca domestica, Stomoxys calcitrans, Haematobia irritans, Lutzomyia shannoni, Lutzomyia* spp., *Phlebotomus* spp., *Fannia canicularis, Hydrotaea aenescens, Calliphora* spp., *Phoenicia* spp., and *Musca autumnalis.*

Application

The pesticidal formulations of the present invention may be dispensed in any conventional manner, for example, from a standard pump-spray container or a pressurized container. In one embodiment, the composition is in a ready-to-use form in which the formulation does not need to be diluted before application. Alternatively, the pesticidal formulation may be in a concentrate form. The concentrate formulation may be diluted by, for example, addition of water.

In one embodiment, the present invention provides a method for controlling or killing insects, comprising contacting an insect with an insecticidally effective amount of a compound or composition/formulation of the present invention.

The amount of formulation of the present invention required to kill pests and the time until death may vary depending on the target species, the composition components, the environment, and the like. For example, CYCLEMONE A™ exhibits higher toxic effects against *An. quadrimaculatus* in comparison to *Aedes aegypti* and *Aedes albopictus.*

The formulation of the present invention can exhibit strong residual toxicity. For instance, filter paper discs impregnated with beta damascone, CYCLEMONE A™ or melafleur emulsified formulation exhibit strong residual toxicity against a variety of insect species, such as, for example, *Musca domestica, Stomoxys calcitrans, Lutzomyia shannoni, Aedes aegypti, Aedes albopictus,* and *Anopheles quadrimaculatus.*

In another embodiment, the formulation of the present invention can be applied on materials such as, for example, papers, wood boards, leathers, adhesives, paints, fabrics, and synthetic materials. For instance, beta damascone, CYCLEMONE A™ or melafleur emulsified formulation applied on ply-wood panel boards exhibits strong toxic effects and residual toxicity against a variety of arthropod species, such as, for example, *Musca domestica, Stomoxys calcitrans, Lutzomyia shannoni, Aedes aegypti, Aedes albopictus,* and *Anopheles quadrimaculatus.*

In another embodiment, the formulations of the present invention can be impregnated into for example, fabrics, tents and nettings. For example, the formulation can be applied on camouflage military fabrics.

Following are examples that illustrate procedures for practicing the invention. These examples should not be construed as limiting. All percentages are by weight and all solvent mixture proportions are by volume unless otherwise noted.

EXAMPLE 1

Chemical Compounds and Formulations

Beta damascone, CYCLEMONE A™, melafleur, citronellol, geranyl acetone, rosalva, and permethrin (99.5%, cis:trans 40:60) can be obtained from sources such as International Flavor & Fragrance, Inc., the Good Scents Company, Bedoukian Research, Inc., and Chem Service, Inc. All of the compounds have listed purity of at least 93%. Formulated (Ectiban 57 g L$^{-1}$ EC) permethrin was obtained from Universal Cooperatives, Minneapolis, Minn.

Six semiochemicals, beta-damascone, CYCLEMONE A™, melafleur, citronellol, geranyl acetone, and rosalva, which have previously been reported as having insecticidal activity, were developed into 500 mL L$^{-1}$ emulsifiable concentrate (EC) formulations. A commercially-available permethrin 57 g L$^{-1}$ EC (Ectiban EC 57; Universal Cooperatives, Minneapolis, Minn.) was included for comparison. Except rosalva, the 50% EC semiochemical formulations were generated by combining 500 mL AI, 430 mL canola oil (Publix, Lakeland, Fla.), 10 mL xylene, 50 mL Triton X-100 (Acros Organics Nev., Fair Lawn, N.J.) and 10 mL Agsolex-8 (International Specialty Products, Wayne, N.J.). The rosalva formulation contained all of the above-mentioned ingredients, with canola oil concentration reduced to 400 mL L$^{-1}$, Triton X-100 concentration increased to 75 mL L$^{-1}$, and 5 mL L$^{-1}$ Antifoam B silicone emulsion (Mallinckrodt Baker, Phillipsburg, N.Y.) included.

EXAMPLE 2

Determination of Toxic Effects of Melafleur, CYCLEMONE A™ and Beta Damascone on *Musca Domestica*

To investigate the toxic effects of melafleur, CYCLEMONE A™ and beta damascone on the house fly, *Musca domestica,* a glass jar contact bioassay is performed.

Briefly, adult house flies, *Musca domestica,* are obtained from strains that have been reared in the laboratory of the Entomology and Nematology Department, University of Florida. The flies are divided into five sets: three sets as the experimental treatments, one set as the positive control, and the other set as the negative control. Each set consists of 20 six-to-ten-day-old adult female flies. Each set of flies in the experiment is exposed to serial dilutions of melafleur, CYCLEMONE A™, or beta damascone in a glass jar. The positive control is exposed to serial dilutions of permethrin. The negative control is not exposed to any chemical compound. The mortality rate is measured after 2-hour, 4-hour, and 24-hour periods. Ataxic flies are considered dead.

The ability of house flies to recover from insecticidal exposure is also investigated. After a 2-hour exposure, each set of flies is transferred into a separate glass jar. The mortality rate is measured at two time intervals: first, immediately at the transfer (2 hours after the initial exposure), and second, 22 hours after the transfer (24 hours after the initial exposure).

The mortality rate is analyzed using the PROBIT model. The data is adjusted based on the mortality rate in the control set using the Abbott's transformation, and the percent mortality is further analyzed based on ANOVA measurement. The experiment is repeated at least three times. The data is discarded if the mortality rate in the control set exceeds 10%. The LC$_{50}$ and LC$_{90}$ values are further determined using the SAS (Cary, N.C., USA) statistical software. For each chemical compound, at least 1280 flies are examined. Each LC value is determined based on data from at least four replications. **, P<0.05.

The results, as shown in Table 1, demonstrate that melafleur, CYCLEMONE A™ and beta damascone exhibit significant toxic effects against the house fly, *Musca domestica*. Specifically, all three compounds result in an almost 100% mortality rate after 24-hour exposure. Among these three compounds, melafleur causes the highest mortality rate both after a 2-hour and a 4-hour exposure period. Furthermore, melafleur, CYCLEMONE A™ and beta damascone exhibit no decline in toxicity after a 24-hour holding period subsequent to an initial 2-hour exposure; whereas, permethrin toxicity declines almost 3 fold.

TABLE 1

Toxic Effects of Melafleur, CYCLEMONE A ™ and Beta Damascone on Susceptible *Musca domestica*

| Exposure period | | LC$_{50}$ (μg cm$^{-2}$) | | | LC$_{90}$ (μg cm$^{-2}$) | | |
|---|---|---|---|---|---|---|---|
| (hours) | Compound | Value | LCL | UCL | Value | LCL | UCL |
| 2 h constant | Beta damascone | 68.85 | 65.42 | 70.92 | 78.46 | 76.66 | 81.12 |
| | Cyclemone A | 48.24 | 44.24 | 51.97 | 69.90 | 64.02 | 79.13 |
| | Melafleur | 34.15 | 28.17 | 39.21 | 91.21 | 74.81 | 127.12 |
| | Permethrin | 0.18 | 0.12 | 0.28 | 1.20 | 0.66 | 3.13 |
| 2 h transferred | Beta damascone | 62.23 | 59.53 | 66.72 | 74.63 | 67.65 | 79.26 |
| | Cyclemone A | 47.29 | 43.28 | 49.83 | 68.95 | 63.11 | 78.96 |
| | Melafleur | 33.21 | 27.26 | 38.54 | 84.56 | 74.32 | 109.27 |
| | Permethrin | 0.58 | 0.44 | 0.86 | 3.56 | 2.98 | 4.95 |
| 4 h constant | Beta damascone | 42.58 | 37.80 | 61.12 | 53.59 | 42.40 | 65.69 |
| | Cyclemone A | 44.52 | 39.42 | 48.84 | 71.44 | 64.75 | 81.87 |
| | Melafleur | 26.38 | 21.46 | 30.27 | 55.75 | 48.83 | 67.72 |
| | Permethrin | 0.10 | 0.07 | 0.14 | 0.95 | 0.56 | 0.59 |
| 24 h constant | Beta damascone | NDR | NDR | NDR | NDR | NDR | NDR |
| | Cyclemone A | NDR | NDR | NDR | NDR | NDR | NDR |
| | Melafleur | NDR | NDR | NDR | NDR | NDR | NDR |
| | Permethrin | 0.03 | 0.02 | 0.04 | 0.41 | 0.25 | 0.82 |

LCL: lower confidence limit;
UCL: upper confidence limit. Serially diluted compounds were applied to glass jars. Insects were exposed to chemicals constantly (2, 4 and 24 h) and mortality rate was assessed. Alternatively, insects were exposed to chemicals for 2 h and were transferred to clean jars with mortality rate assessed 24 h after initial exposure.

EXAMPLE 3

Determination of Toxic Effects of Melafleur, CYCLEMONE A™ and Beta Damascone on Field-Collected *Musca domestica*

To investigate the toxic effects of melafleur, CYCLEMONE A™ and beta damascone on the field-collected house fly, *Musca domestica,* a glass jar contact bioassay is performed.

Briefly, one *Musca domestica* strain is collected from the University of Florida dairy unit in Alachua County, Florida, U.S.A. ("the Alachua strain"). The other *Musca domestica* strain is collected from a dairy farm in Gilchrist County, Florida, U.S.A. ("the Gilchrist strain"). Both strains are colonized adults, and are subsequently reared at 27° C. in the laboratory of the Entomology and Nematology Department, University of Florida.

Each strain is further divided into five sets: three sets as the experimental treatments, one set as the positive control, and the other set as the negative control. Each set consists of 20 six-to-ten-day-old adult female flies. The experimental sets are exposed to serial dilutions of melafleur, CYCLEMONE A™ or beta damascone in a glass jar. The positive control is exposed to serial dilutions of permethrin. The negative control is not exposed to any chemical compound. 1 mL of insecticide was dissolved in acetone (concentrations between 0.5 and 20 mg mL$^{-1}$) in a 60 mL glass jar having a 67.86 cm$^2$ inside surface area (Wheaton, Millville, N.J.). Jars were allowed to dry for 1 h prior to fly introduction. Flies were held in jars for 2, 4 and 24 h, and fly mortality rate was scored at that time. Sugar water (10%) was provided in all assays, unless stated otherwise. The mortality rate is measured after a 2-hour, 4-hour, and 24-hour period. Ataxic flies are considered dead. The mortality rate and the LC values are determined using the same procedures as is illustrated in Example 2.

The results, as shown in Table 2, demonstrate that melafleur, CYCLEMONE A™ and beta damascone exhibit significant toxic effects against field-collected *Musca domestica*. Among these three compounds, melafleur causes the highest mortality rate on both strains.

EXAMPLE 4

Determination of Toxic Effects of Melafleur, CYCLEMONE A™ and Beta Damascone on Field-Collected *Stomoxys calcitrans*

To investigate the toxic effects of melafleur, CYCLEMONE A™ and beta damascone on the field-collected stable fly, *Stomoxys calcitrans*, a glass jar contact bioassay method is performed.

Briefly, one *Stomoxys calcitrans* strain is collected from the University of Florida dairy unit in Alachua County, Florida, U.S.A. ("the Alachua strain") and subsequently reared at 27° C. in the laboratory of the Entomology and Nematology Department, University of Florida.

Each strain is divided into four sets: three sets as the experimental treatments and the other set as the control. Each set consists of 20 six-to-ten-day-old adult female flies. The experimental set is exposed to serial dilutions of melafleur, CYCLEMONE A™ or beta damascone in a glass jar. The control set is not exposed to any chemical compound. The mortality rate is measured after a 2-hour, 4-hour, and 24-hour period. Ataxic flies are considered dead. The mortality rate and the LC values are determined using the same procedures as is illustrated in Example 2.

The results, as shown in Table 3, demonstrate that melafleur, CYCLEMONE A™ and beta damascone exhibit significant toxic effects against field-collected *Stomoxys calcitrans*. In comparison to house flies, all three compounds exhibit greater toxicity against stable flies (Lower LC values).

TABLE 2

Toxic Effects of Melafleur, CYCLEMONE A ™ and Beta Damascone on Field-collected *Musca domestica*

| Exposure period (hours) | Fly strain | Semiochemical | LC$_{50}$ (µg cm$^{-2}$) | | | LC$_{90}$ (µg cm$^{-2}$) | | |
|---|---|---|---|---|---|---|---|---|
| | | | Value | LCL | UCL | Value | LCL | UCL |
| 2 h constant | Gilchrist | Beta damascone | 78.84 | 66.18 | 91.37 | 126.00 | 106.10 | 177.58 |
| | | Cyclemone A | 54.11 | 49.29 | 57.50 | 72.60 | 68.78 | 78.25 |
| | | Melafleur | 47.58 | 44.34 | 51.05 | 80.90 | 72.71 | 75.70 |
| | | Permethrin | 0.41 | 0.27 | 0.61 | 1.82 | 1.11 | 4.03 |
| | Alachua | Beta damascone | 77.37 | 66.39 | 89.53 | 136.39 | 114.50 | 187.52 |
| | | Cyclemone A | 54.46 | 49.57 | 57.99 | 74.41 | 70.45 | 80.23 |
| | | Melafleur | 45.45 | 41.96 | 49.08 | 83.26 | 74.11 | 98.35 |
| | | Permethrin | 4.61 | 3.18 | 8.45 | 14.86 | 8.20 | 66.96 |
| 4 h constant | Gilchrist | Beta damascone | 52.01 | 46.27 | 55.78 | 70.59 | 66.71 | 76.34 |
| | | Cyclemone A | 46.52 | 43.32 | 49.91 | 79.28 | 71.35 | 75.50 |
| | | Melafleur | 37.84 | 35.12 | 40.49 | 59.98 | 54.90 | 67.53 |
| | | Permethrin | 0.39 | 0.33 | 0.46 | 1.51 | 1.19 | 2.03 |
| | Alachua | Beta damascone | 76.22 | 62.34 | 89.53 | 124.69 | 103.53 | 183.62 |
| | | Cyclemone A | 52.60 | 47.32 | 56.10 | 69.96 | 66.25 | 75.59 |
| | | Melafleur | 39.91 | 37.29 | 42.49 | 62.39 | 57.29 | 70.02 |
| | | Permethrin | 4.10 | 2.90 | 6.79 | 15.85 | 8.77 | 53.60 |
| 24 h constant | Gilchrist | Beta damascone | 40.02 | 14.81 | 48.08 | 56.21 | 44.67 | 61.80 |
| | | Cyclemone A | 32.32 | 29.81 | 34.65 | 51.58 | 47.29 | 58.11 |
| | | Melafleur | 32.91 | 25.60 | 39.80 | 59.29 | 48.42 | 81.87 |
| | | Permethrin | 0.16 | 0.13 | 0.20 | 0.85 | 0.66 | 1.19 |
| | Alachua | Beta damascone | 27.34 | 23.82 | 30.69 | 47.00 | 41.37 | 55.76 |
| | | Cyclemone A | 32.29 | 28.91 | 34.18 | 51.09 | 46.77 | 57.64 |
| | | Melafleur | 35.25 | 24.32 | 45.74 | 53.01 | 38.96 | 59.83 |
| | | Permethrin | 0.99 | 0.84 | 1.18 | 3.78 | 2.89 | 5.39 |

LCL: lower confidence limit;
UCL: upper confidence limit. Serially diluted compounds were applied to glass jars. Insects were exposed to chemicals constantly (2, 4 and 24 h) and mortality rate was assessed. Alternatively, insects were exposed to chemicals for 2 h and were transferred to clean jars with mortality rate assessed 24 h after initial exposure.

TABLE 3

Toxic Effects of Melafleur, CYCLEMONE A ™ and Beta Damascone on *Stomoxys calcitrans*

| Exposure period (hours) | Semiochemical | LC$_{50}$ ($\mu$g cm$^{-2}$) | | | LC$_{90}$ ($\mu$g cm$^{-2}$) | | |
|---|---|---|---|---|---|---|---|
| | | Value | LCL | UCL | Value | LCL | UCL |
| 2 h constant | Beta damascone | 19.74 | 10.53 | 26.49 | 34.57 | 25.87 | 94.78 |
| | Cyclemone A | 19.52 | 17.41 | 21.48 | 31.31 | 28.19 | 35.95 |
| | Melafleur | 18.19 | 15.78 | 20.45 | 36.13 | 31.90 | 42.29 |
| 4 h constant | Beta damascone | 18.07 | 8.74 | 23.36 | 29.68 | 22.16 | 72.78 |
| | Cyclemone A | 18.18 | 16.03 | 20.22 | 32.38 | 28.80 | 37.66 |
| | Melafleur | 16.39 | 14.19 | 18.45 | 31.33 | 27.60 | 36.84 |
| 24 h constant | Beta damascone | 11.33 | 9.50 | 12.90 | 20.33 | 18.01 | 23.68 |
| | Cyclemone A | 14.82 | 12.87 | 16.69 | 27.10 | 23.77 | 32.25 |
| | Melafleur | 11.81 | 10.49 | 13.14 | 19.10 | 16.91 | 22.53 |

LCL: lower confidence limit,
UCL: upper confidence limit. Serially diluted compounds were applied to glass jars. Insects were exposed to chemicals constantly (2, 4 and 24 h) and mortality rate was assessed. Alternatively, insects were exposed to chemicals for 2 h and were transferred to clean jars with mortality rate assessed 24 h after initial exposure.

EXAMPLE 5

Determination of Toxic Effects of Melafleur, CYCLEMONE A™ and Beta Damascone on *Aedes aegypti*

To investigate the toxic effects of melafleur, CYCLEMONE A™ and beta damascone on yellow fever mosquito, *Ae. aegypti*, a glass jar contact bioassay is performed.

First, the toxic effects of melafleur, CYCLEMONE A™ and beta damascone applied on filter paper discs are examined. Briefly, yellow fever mosquito, *Ae. aegypti* were obtained from strains that have been cultured in the laboratory of the Entomology and Nematology Department, University of Florida.

The mosquitoes are divided into five sets: three sets as the experimental set, one set as the positive control, and the other set as the negative control. Each set consists of 20 six-to-ten-day old adult females. Each set is placed into a 60 ml glass jar, fitted with 17.34 cm$^2$ Whatman No. 1 filter paper discs impregnated with 0.5 ml melafleur, CYCLEMONE A™ or beta damascone serially diluted in an acetone solution (the experiment), permethrin serially diluted in acetone (the positive control), or acetone-only (the negative control). The mortality rate is measured after a 2-hour, 4-hour and 24-hour exposure period. Ataxic mosquitoes are considered dead.

The ability of *Ae. aegypti* to recover from insecticidal exposure is also investigated. After a 2-hour exposure, each set of *Ae. aegypti* is transferred into a separate jar. The mortality rate is measured at two time intervals: first, immediately at the transfer (2 hours after the initial exposure), and second, 22 hours after the transfer (24 hours after the initial exposure).

In addition, the toxic effects of melafleur, CYCLEMONE A™ and beta damascone formulations applied on camouflage military fabric are examined according to the same procedures as described above. The mortality rate and the LC values are determined using the same procedures as is illustrated in Example 2.

The results, as shown in Table 4, demonstrate that melafleur, CYCLEMONE A™ and beta damascone applied on filter paper discs or camouflage military fabric exhibit significant toxic effects against susceptible *Ae. aegypti*. Specifically, all three compounds, applied either on filter paper discs or camouflage military fabric, result in an almost 100% mortality rate after a 24-hour exposure. Among the three compounds, CYCLEMONE A™ causes the highest mortality rate both after a 2-hour and 4-hour exposure period.

TABLE 4

Toxic Effects of Melafleur, CYCLEMONE A ™ and Beta Damascone on *Aedes aegypti*

| | | LC$_{50}$ ($\mu$g cm$^{-2}$) | | | | | |
|---|---|---|---|---|---|---|---|
| | | On filter paper | | | On camouflage military fabric | | |
| Exposure period (hours) | Semiochemical | Value | LCL | UCL | Value | LCL | UCL |
| 2 h constant | Beta damascone | 47.81 | 45.78 | 49.90 | 38.26 | 32.63 | 47.39 |
| | Cyclemone A | 26.01 | 23.63 | 30.01 | 26.03 | 22.26 | 30.69 |
| | Melafleur | 27.48 | 25.78 | 29.04 | 29.36 | 22.93 | 33.91 |
| | Permethrin | 0.02 | 0.01 | 0.10 | 0.012 | 0.008 | 0.042 |
| 2 h transferred | Beta damascone | 35.27 | 30.65 | 38.41 | 6.39 | 58.93 | 61.27 |
| | Cyclemone A | 18.98 | 13.87 | 33.12 | 41.13 | 32.43 | 52.26 |
| | Melafleur | 22.83 | 21.79 | 23.91 | 37.59 | 31.09 | 43.24 |
| | Permethrin | 0.04 | 0.02 | 0.14 | 0.45 | 0.21 | 1.89 |
| 4 h constrant | Beta damascone | 35.27 | 30.65 | 38.41 | 31.36 | 23.12 | 38.54 |
| | Cyclemone A | 18.98 | 13.87 | 33.12 | 17.23 | 12.63 | 23.52 |
| | Melafleur | 22.83 | 21.79 | 23.91 | 19.84 | 16.64 | 28.63 |
| | Permethrin | 0.0018 | 0.0016 | 0.0021 | 0.0009 | 0.0007 | 0.0017 |
| 24 hr constant | Beta damascone | NDR | NDR | NDR | NDR | NDR | NDR |
| | Cyclemone A | NDR | NDR | NDR | NDR | NDR | NDR |
| | Melafleur | NDR | NDR | NDR | NDR | NDR | NDR |
| | Permethrin | 0.00045 | 0.00032 | 0.00045 | 0.00031 | 0.00023 | 0.00045 |

LCL: lower confidence limit,
UCL: upper confidence limit. Serially diluted compounds were applied to glass jars.

NDR = appropriate dose-response curves could not be generated. Insects were exposed to chemicals constantly (2, 4 and 24 h) and mortality rate was assessed. Alternatively, insects were exposed to chemicals for 2 h and were transferred to clean jars with mortality rate assessed 24 h after initial exposure.

EXAMPLE 6

Determination of Toxic Effects of Melafleur, CYCLEMONE A™ and Beta Damascone on *Anopheles quadrimaculatus* and *Aedes albopictus*

To investigate the toxic effects of melafleur, CYCLEMONE A™ and beta damascone on *Anopheles quadrimaculatus* (Say) and *Ae. albopictus* (Skuse), a contact bioassay is performed.

Briefly, *Anopheles quadrimaculatus* (Say) is obtained from the United States Department of Agriculture, ARS, Center for Medical, Agricultural and Veterinary Entomology, Gainesville, Fla., and adults are held in the laboratory of the Entomology and Nematology Department, University of Florida with no insecticide exposure or introduction of other insects. The Asian tiger mosquito, *Ae. albopictus* (Skuse) is obtained from a laboratory colony of the Entomology and Nematology Department, University of Florida.

Each strain is divided into four sets: three sets as the experiment and the other set as the control. Each set consists of 20 six-to-ten-day-old adult female mosquitoes. Each set is placed into a 60 ml glass jar, fitted with 17.34 $cm^2$ Whatman No. 1 filter paper discs impregnated with 0.5 ml serial dilution of melafleur, CYCLEMONE A™ or beta damascone acetone solution (the experiment) or acetone (the control). The mortality rate is measured after a 2-hour, 4-hour, and 24-hour exposure period. Ataxic mosquitoes are considered dead. The mortality rate and the LC values are determined using the same procedures as is illustrated in Example 2.

The results, as shown in Table 5, demonstrate that melafleur, CYCLEMONE A™ and beta damascone exhibit significant toxic effects against *Anopheles quadrimaculatus* and *Aedes albopictus*. Among the three compounds, CYCLEMONE A™ causes the highest mortality rate on *An. quadrimaculatus*; while melafleur results in the highest mortality rate on *Ae. albopictus*. All mosquitoes were dead at the 24-hour examination.

TABLE 5

Toxic Effects of Melafleur, CYCLEMONE A™ and Beta Damascone on *Anopheles quadrimaculatus* and *Aedes albopictus*

| Exposure period (hours) | Semiochemical | $LC_{50}$ ($\mu g\, cm^{-2}$) | | | | | |
|---|---|---|---|---|---|---|---|
| | | *An. quadrimaculatus* | | | *Ae. albopictus* | | |
| | | Value | LCL | UCL | Value | LCL | UCL |
| 2 h constant | Beta damascone | 32.19 | 19.96 | 44.55 | 25.18 | 14.56 | 35.82 |
| | Cyclemone A | 14.29 | 12.80 | 15.74 | 19.88 | 18.47 | 21.24 |
| | Melafleur | 27.03 | 25.07 | 28.76 | 19.34 | 16.51 | 21.82 |
| 4 h constant | Beta damascone | 15.43 | 12.11 | 18.14 | 23.06 | 13.85 | 32.77 |
| | Cyclemone A | 12.27 | 9.98 | 33.12 | 18.72 | 17.25 | 20.10 |
| | Melafleur | 22.90 | 21.37 | 24.16 | 13.22 | 12.14 | 14.22 |

LCL: lower confidence limit,
UCL: puper confidence limit. Values are $LC_{50}$ 95% CL ($\mu g\, cm-2$). Serially diluted compounds were applied to glass jars. Insects were exposed to chemicals constantly (2, 4 and 24 h) and mortality rate was assessed. Alternatively, insects were exposed to chemicals for 2 h and were transferred to clean jars with mortality rate assessed 24 h after initial exposure.

EXAMPLE 7

Determination of Toxic Effects of Melafleur, CYCLEMONE A™ and Beta Damascone on *Lutzomyia shannoni*

To investigate the toxic effects of melafleur, CYCLEMONE A™ and beta damascone on the sand fly, *Lutzomyia shannoni*, a contact bioassay is performed.

Briefly, the sand fly, *Lutzomyia shannoni* (Dyar) was collected from the San Felasco State Reserve Park, Gainesville, Fla. using Mosquito Magnet-X traps as described in Mann et al. (Mann R S, Kaufman P E and Butler J F, *Lutzomyia* spp. (Diptera: Psychodidae) response to olfactory attractant- and light emitting diode-modified Mosquito Magnet X (MM-X) traps. *J Med Entomol* 46: 1052-1061 (2009)). The sand flies are divided into five sets: three sets as the experimental set, one set as the positive control, and the other set as the negative control. Each set consists of 20, six-to-ten-day old adult flies. Each set is placed into a 60 ml glass jar, fitted with 17.34 $cm^2$ Whatman No. 1 filter paper discs impregnated with 0.5 ml serial dilutions of melafleur, CYCLEMONE A™ or beta damascone acetone solution (the experiment), permethrin (the positive control), or acetone (the negative control). The mortality rate is measured after a 2-hour exposure period. Ataxic flies are considered dead. The mortality rate is determined using the same procedures as is illustrated in Example 2.

The results demonstrate that melafleur, CYCLEMONE A™ and beta damascone are extremely toxic against *Lutzomyia shannoni*. All *Lu. shannoni* were dead after being exposed to melafleur, CYCLEMONE A™ and beta damascone at a concentration of 27.03, 14.29, and 32.19 $\mu g\, cm^{-2}$ (the respective $LC_{50}$ values of melafleur, CYCLEMONE A™ and beta damascone against *Aedes albopictus* after a 2-hour exposure), respectively.

EXAMPLE 8

Determination of Toxic Effects of Melafleur, CYCLEMONE A™ and Beta Damascone Formulations on *Musca domestica*

To investigate the toxic effects of melafleur, CYCLEMONE A™ and beta damascone formulations on the house fly, *Musca domestica*, a contact bioassay is performed according to the following procedures.

Briefly, Whatman No. 1 filter paper discs (63.58 $cm^2$) are impregnated with 1.5 ml serially diluted formulations in 20 emulsified concentrates and 50 emulsified concentrates, respectively, and subsequently dried for about an hour. Then, house flies are divided into seven sets: three sets as the experiment, three sets as the positive control, and one set as the negative control. Each set consists of twenty six-to-ten-day old adult flies. The experiment set is placed in an exposure container containing filter paper discs impregnated with melafleur, CYCLEMONE™ or beta damascone for a period of 24-hour and 48-hour. The positive control set is exposed to paper discs impregnated with geranyl acetone, rosalva or citronellol. The negative control set is exposed to paper discs impregnated with acetone solution. Throughout the exposure periods, each set is provided with 10% sucrose solution and sufficient air circulation. Ataxic flies are considered dead. The mortality rate and the LC values are determined using the same procedures as is illustrated in Example 2.

The results, as shown in Table 6, demonstrate that melafleur, CYCLEMONE A™ and beta damascone formulations exhibit significant toxic effects against *Musca domestica*. Among three formulations, melafleur formulation results in the highest mortality rate both after a 24-hour and 48-hour exposure periods. Furthermore, compared to the toxicity after a 24-hour exposure period, the toxicity of melafleur formulation doubles after 48 hours.

In comparison with previously known semiochemicals having insecticidal activity, such as geranyl acetone, rosalva or citronellol, melafleur, CYCLEMONE A™ and beta damascone formulations result in a higher mortality rate at a lower concentration. For example, a melafleur formulation is 2 times more toxic than a geranyl acetone formulation and 4 times more toxic than a citronellol formulation.

TABLE 6

Toxic Effects Melafleur, CYCLEMONE A ™ and Beta Damascone Formulations on Susceptible *Musca domestica*

| Exposure period (hours) | Semiochemical | $LC_{50}$ 95% CL ($\mu g \, cm^{-2}$) | | | $LC_{99}$ 95% CL ($\mu g \, cm^{-2}$) | | |
|---|---|---|---|---|---|---|---|
| | | Value | LCL | UCL | Value | LCL | UCL |
| 24 | Beta damascone | 413.32 | 317.04 | 505.44 | 618.12 | 713.96 | 1533.68 |
| | Cyclemone A | 468.96 | 438.8 | 499.08 | 759.00 | 697.32 | 847.68 |
| | Melafleur | 312.44 | 243.28 | 366.12 | 808.04 | 704.24 | 990.48 |
| | Citronellol | 560.20 | 450.44 | 693.56 | 580.00 | 481.24 | 1110.6 |
| | Geranyl acetone | 711.16 | 489.72 | 1102.16 | 1227.00 | 881.04 | 1431.16 |
| | Rosalva | 529.04 | 362.36 | 702.04 | 1054.32 | 772.20 | 1896.68 |
| 48 | Beta damascone | 372.40 | 351.04 | 392.56 | 516.16 | 482.8 | 566.12 |
| | Cyclemone A | 440.04 | 414.24 | 465.52 | 659.92 | 611.16 | 731.6 |
| | Melafleur | 133.60 | 35.28 | 211.76 | 416.44 | 308.00 | 193.64 |
| | Citronellol | 553.48 | 454.72 | 668.4 | 886.04 | 698.00 | 1407.88 |
| | Geranyl acetone | 541.96 | 285.84 | 811.52 | 716.72 | 643.88 | 1450.36 |
| | Rosalva | 517.44 | 351.96 | 659.76 | 1022.88 | 771.56 | 2191.28 |

LCL: lower confidence limit,
UCL: upper confidence limit. Serially diluted compounds were applied to filter papers. Mortality rate was assessed after constant exposure for the prescribed period.

EXAMPLE 9

Determination of Residual Toxicity of Melafleur, CYCLEMONE A™ and Beta Damascone Formulations on *Musca domestica*

To investigate the residual toxicity of melafleur, CYCLEMONE A™ and beta damascone formulations on the house fly, *Musca domestica*, a residual contact bioassay is performed according to the following procedures.

Briefly, after *Musca domestica* is exposed to formulations for 24 hours at the $LC_{99}$ concentration specific for each compound, each set of flies is transferred into a separate glass jar, and held for another 24 hours when mortality is scored. The mortality rate is measured on multiple days with new sets of flies up to 14 days (Day 1 starts at 24 hours after the transfer). The mortality rate is determined using the same procedures as is illustrated in Example 2. The results, as shown in Table 7, demonstrate that melafleur, CYCLEMONE A™ and beta damascone formulations exhibit significant residual toxicity against the house fly, *Musca domestica*. Specifically, melafleur, CYCLEMONE A™ and beta damascone formulations result in a 99% mortality rate on Day 1 and Day 2.

In comparison with formulations composed of geranyl acetone, rosalva or citronellol, melafleur, CYCLEMONE A™ and beta damascone formulations exhibit a higher residual toxicity for a longer period of time. Eight days after the initial exposure, melafleur, CYCLEMONE A™ and beta damascone formulations still exhibit residual toxicity; however, the citronellol formulation only exhibits a weak toxic effect, while rosalva and geranyl acetone formulations are no longer toxic.

TABLE 7

Residual Toxicity of Melafleur, CYCLEMONE A ™ and Beta Damascone Formulations susceptible *Musca domestica*

| Semiochemical | Concentration (mg cm$^{-2}$) | % mortality on various days following treatment | | | | | | |
|---|---|---|---|---|---|---|---|---|
| | | 1 | 2 | 3 | 5 | 7 | 8 | 14 |
| Beta damascone | 0.76 | 97.50a | 91.25a | 81.25a | 70.00ab | 58.75a | 51.25a | 8.75ab |
| Citronellol | 1.30 | 93.75a | 86.25a | 82.50a | 62.50b | 38.75b | 22.50b | 3.75ab |
| Cyclemone A | 1.11 | 96.25a | 90.00a | 80.00a | 77.50ab | 78.75a | 63.75a | 6.25ab |
| Geranyl acetone | 1.91 | 97.50a | 83.75a | 47.50b | 21.25c | 8.75c | 2.50c | 6.25ab |
| Melafleur | 0.77 | 98.75a | 95.00a | 85.00a | 86.25a | 57.50a | 55.00a | 12.5a |
| Rosalva | 1.85 | 93.75a | 95.00a | 61.25b | 32.50c | 17.50c | 7.50c | 2.50b |
| Control | — | 1.25b | 3.75b | 0.00c | 1.25d | 0.00d | 2.50c | 5.00ab |

Within a column, mortality mean followed by different letters are significantly different (p<0.05). Concentrations were generated from technical-based $LC_{99}$ values obtained following a 24 h-exposure period on filter paper. Paper was treated on day 0 and was held until exposure on post-treatment day. Control contained formulation ingredients without semiochemicals.

EXAMPLE 10

Determination of Toxic Effect of Melafleur, CYCLEMONE A™ and Beta Damascone Formulations on *Ae. aegypti*

To investigate the toxic effects of melafleur, CYCLEMONE A™ and beta damascene emulsified concentrate formulations applied on camouflage military fabric against *Ae. aegypti*, a contact bioassay is performed according to the following procedures.

Briefly, a piece of 10×10 cm$^2$ fabric (TenCate Defender™) is impregnated with 2 ml of serially diluted 20-emulsifiable concentrate or 50-emulsifiable concentrate formulations, respectively, and subsequently dried for about an hour. Also, six-to-ten-day-old, never blood-fed, adult female *Ae. aegypti* mosquitoes are obtained. The mosquitoes are divided into seven sets: three sets as the experiment, three sets as the positive control, and one set as the negative control. Each set consists of 20 mosquitoes. The experiment set is placed into a mesh bag containing the fabric pieces treated with melafleur, CYCLEMONE A™ or beta damascone for a period of 2 hours, 4 hours and 24 hours. The positive control set is exposed to fabric pieces treated with geranyl acetone, rosalva or citronellol. The negative control set is exposed to fabric pieces treated with acetone solution. Throughout the exposure periods, each set is provided with 10% sucrose solution and sufficient air circulation. Ataxic mosquitoes are considered dead. The mortality rate and the LC values are determined using the same procedures as are illustrated in Example 2.

The results, as shown in Table 8, demonstrate that melafleur, CYCLEMONE A™ and beta damascone formulations exhibit significant toxicity against *Ae. aegypti*. Compared to formulations composed of citronellol, geranyl acetone and rosalva, melafleur, CYCLEMONE A™ and beta damascone emulsified concentrate formulations exhibit higher toxicity against *Ae. aegypti*. Specifically, the melafleur formulation exhibits the highest toxic effects.

TABLE 8

Toxic Effects of Melafleur, CYCLEMONE A ™ and Beta Damascone Formulations on *Aedes aegypti*

| Exposure period (hours) | Semiochemical | $LC_{50}$ ($\mu g\, cm^{-2}$) | | | $LC_{90}$ ($\mu g\, cm^{-2}$) | | |
|---|---|---|---|---|---|---|---|
| | | Value | LCL | UCL | Value | LCL | UCL |
| 2 | Beta damascone | 296.28 | 254.35 | 352.26 | 910.52 | 682.35 | 1422.61 |
| | Citronellol | 324.09 | 258.42 | 438.85 | 1938.19 | 1124.67 | 5252.00 |
| | Cyclemone A | 180.23 | 168.11 | 214.23 | 452.11 | 378.13 | 580.23 |
| | Geranyl acetone | 318.87 | 242.84 | 470.62 | 934.62 | 588.68 | 2782.08 |
| | Melafleur | 176.05 | 118.26 | 252.53 | 588.26 | 624.34 | 2012.56 |
| | Rosalva | 384.11 | 322.39 | 482.45 | 1276.16 | 896.19 | 2272.02 |
| 4 | Beta damascone | 250.45 | 224.23 | 292.43 | 648.16 | 524.23 | 888.62 |
| | Citronellol | 266.44 | 218.56 | 342.73 | 1434.18 | 906.23 | 3218.82 |
| | Geranyl acetone | 254.13 | 188.62 | 366.34 | 742.61 | 474.01 | 2146.91 |
| | Cyclemone A | 172.56 | 148.11 | 198.06 | 488.13 | 396.26 | 658.09 |
| | Melafleur | 146.62 | 122.43 | 170.84 | 460.14 | 368.53 | 636.24 |
| | Rosalva | 364.74 | 306.32 | 456.28 | 1262.11 | 880.11 | 2264.79 |
| 24 | Beta damascone | 208.37 | 148.26 | 294.00 | 534.26 | 358.62 | 1410.62 |
| | Citronellol | 236.11 | 174.75 | 336.81 | 700.43 | 450.38 | 1980.81 |
| | Cyclemone A | 136.19 | 118.17 | 154.23 | 330.22 | 278.56 | 418.34 |
| | Geranyl acetone | 132.29 | 114.46 | 152.36 | 338.61 | 284.43 | 432.22 |
| | Melafleur | 124.62 | 88.91 | 162.06 | 362.35 | 260.08 | 686.53 |
| | Rosalva | 168.21 | 144.34 | 196.67 | 500.92 | 402.29 | 686.72 |

LCL: lower confidence limit,
UCL: upper confidence limit. Insects were exposed to chemicals for 2 h and mortality rate was assessed immediately. Flies were subsequently held in clean jars and mortality rate was reassessed 4 and 24 h after initial exposure.

EXAMPLE 11

Determination of the Residual Toxicity of Melafleur, CYCLEMONE A™ and Beta Damascone Formulations on *Ae. aegypti*

To investigate the residual toxicity of melafleur, CYCLEMONE A™ and beta damascone formulations applied on camouflage military fabrics against the yellow fever mosquito, *Ae. aegypti*, a residual contact bioassay is performed according to the following procedures.

Briefly, after mosquitoes are exposed to formulations for 2 hours at a concentration of $LC_{99}$, each set is transferred into a separate glass jar, and held for another 24 hours. The mortality rate is measured with new mosquitoes on post-treatment days 2, 3, 5, 8 and 14 (Day 1 starts at 24 hours after the transfer), and is determined using the same procedures as are illustrated in Example 2.

The results, as shown in Table 9, demonstrate that melafleur, CYCLEMONE A™ and beta damascone formulations exhibit significant residual effect against *Ae. aegypti*. Specifically, all three formulations result in a high mortality rate of above 90% on the first two days. Compared to citronellol, geranyl acetone, and rosalva they also demonstrate a significantly higher residual toxicity.

TABLE 9

Residual Toxicity of Melafleur, CYCLEMONE A ™ and Beta Damascone Formulations on *Aedes aegypti*

| Semiochemical | Concentration (mg cm$^{-2}$) | % mortality on various days following treatment | | | | | |
|---|---|---|---|---|---|---|---|
| | | 1 | 2 | 3 | 5 | 8 | 14 |
| Beta damascone | 2.27 | 95.00a | 90.00a | 72.50ab | 62.50a | 22.50b | 0.00d |
| Citronellol | 3.22 | 95.00a | 77.50a | 62.50b | 35.00b | 22.50b | 2.50cd |
| Cyclemone A | 1.12 | 100.00a | 97.50a | 92.50a | 75.00a | 25.50ab | 17.50a |
| Geranyl acetone | 2.24 | 91.25a | 83.00a | 30.00c | 32.50b | 17.50c | 5.00c |
| Melafleur | 1.66 | 100.00a | 95.00a | 85.00a | 65.00a | 17.50c | 12.50b |
| Rosalva | 3.39 | 95.00a | 87.50a | 65.00b | 35.00b | 27.50a | 0.00d |
| Control | — | 2.25b | 5.00b | 2.50d | 7.25c | 4.50d | 2.50cd |

Within a column, mortality mean followed by different letters are significantly different (p<0.05). Concentrations were generated from technical-based LC$_{99}$ values obtained from a 2 h exposure period on military fabric. Fabric was treated on day 0 and was held until exposure on post-treatment day. Mosquitoes were exposed for 2 h, and mortality rate was assessed 24 h after initial exposure. Control contained formulation ingredients without semiochemicals.

EXAMPLE 12

Determination of Toxic Effects of Melafleur, CYCLEMONE A™ and Beta Damascone Formulations Applied on Ply-Wood Panel Boards Against *Musca domestica* and *Stomoxys calcitrans*

To investigate the toxic effects of melafleur, CYCLEMONE A™ and beta damascone formulations applied on ply-wood boards against the house fly, *Musca domestica* and the stable fly, *Stomoxys calcitrans*, a contact bioassay is performed according to the following procedures.

Briefly, each fly strain is divided into eight sets: three sets as the experiment, four sets as the positive control, and one set as the negative control. Flies are assayed on unpainted ply-wood panel boards that have been previously exposed to natural summer weather conditions for at least 10 days. In the experimental set, a melafleur, CYCLEMONE A™ or beta damascone formulation is applied to the panels at a concentration of 1.67 mg/cm$^2$. The positive control set is treated with permethrin, geranyl acetone, rosalva or citronellol. The negative control set is treated with water. The formulation is applied at a uniform rate of 7.5 ml per 225 cm$^2$, sufficient to cover the entire panel without dripping. Subsequently, the treated panel boards are dried for about an hour.

In each set, 20 adult flies are placed onto the panel boards. Flies are secured with wooden embroidery hoops, covered with a coarse mesh screen cloth previously sprayed with the respective formulation. After 4 hours, flies are transferred into a clean jar. The mortality rate is measured 24 hours after the transfer, and is determined using the same procedures as are illustrated in Example 2.

The results, as shown in Table 10, demonstrate that melafleur, CYCLEMONE A™ and beta damascone formulations applied on ply-wood panel boards exhibit significant toxic effects against the house fly, *Musca domestica*, and the stable fly, *Stomoxys calcitrans*. Specifically, melafleur, CYCLEMONE A™ and beta damascone formulations result in 99-100% mortality rate on the stable fly, *Stomoxys calcitrans*, whereas conventional insecticidal semiochemicals such as citronellol, geranyl acetone and rosalva formulations only exhibit weak toxic effects.

TABLE 10

Toxic Effects of Melafleur, CYCLEMONE A ™ and Beta Damascone Formulations Applied on Ply-wood Panel Boards against *Musca domestica* and *Stomoxys calcitrans*

| | % mortality | |
|---|---|---|
| Semiochemical | *M. domestica* | *S. calcitrans* |
| Beta damascone | 29.20c | 99.00a |
| Citronellol | 0.62d | 43.33b |
| Cyclemone A | 48.20b | 100.00a |
| Geranyl acetone | 0.29d | 41.67b |
| Melafleur | 50.40b | 100.00a |
| Rosalva | 3.10d | 50.00b |
| Permethrin | 88.40a | 100.00a |
| Control | 2.20d | 5.83d |

Within a column, mortality means followed by different letters are significantly different (p<0.05). Plywood panels (225 cm$^2$) were treated with chemicals at a rate of 1.67 mgcm$^{-2}$. Panels were treated on day 0 and held until exposure on post-treatment day. Mosquitoes were exposed to chemicals for 2 h, and mortality rate was assessed 24 h after initial exposure. Control contained formulation ingredients without semiochemicals.

EXAMPLE 13

Determination of the Residual Toxicity of Melafleur, CYCLEMONE A™ and Beta Damascone Formulations Applied on Ply-Wood Panel Boards Against *Musca domestica*

To investigate the residual toxicity of melafleur, CYCLEMONE A™ and beta damascone formulations applied on ply-wood panel boards against the house fly, *Musca domestica*, a residual contact bioassay is performed according to the following procedures.

Briefly, after *Musca domestica* is exposed to formulations at concentration of 3.33 mg cm$^{-2}$ for 2 hours, each set is transferred into a separate glass jar, and held for another 24 hours. The residual effectiveness of the compounds is measured by the mortality observed by exposure of new *Musca domestica* on post-treatment Days 2, 3, 5, 7 and 14 (Day 1 starts at 24 hours after the transfer), and is determined using the same procedures as are illustrated in Example 2.

The results, as shown in Table 11, demonstrate that melafleur, CYCLEMONE A™ and beta damascone formulations applied on ply-wood panel boards exhibit significant residual toxicity against *Musca domestica*. Compared to formulations composed of citronellol, geranyl acetone or rosalva, all three formulations applied on panel boards exhibit significantly higher residual toxicity. Specifically, citronellol and rosalva formulations exhibit no residual toxicity against *Musca domestica*. While the geranyl acetone formulation has weak residual toxicity on Day 1, it loses toxic effects thereafter.

TABLE 11

Residual Toxicity of Melafleur, CYCLEMONE A ™ and Beta Damascone Formulations Applied on Ply-wood Panel Boards against *Musca domestica*

| Semiochemical | % mortality on various days following treatment | | | | | |
|---|---|---|---|---|---|---|
| | 1 | 2 | 3 | 5 | 7 | 14 |
| Beta damascone | 100.00a | 30.75c | 28.50c | 20.50c | 15.75b | 3.00b |
| Citronellol | 0.00c | 0.00d | 0.00d | 0.00d | 0.00c | 0.00b |
| Cyclemone A | 100.00a | 49.25b | 48.25b | 27.75c | 18.75b | 9.00b |
| Geranyl acetone | 33.50b | 0.00d | 0.00d | 0.00d | 0.00c | 0.00b |
| Melafleur | 100.00a | 59.50b | 46.00b | 44.75b | 25.75b | 8.50b |
| Rosalva | 0.00c | 0.00d | 0.00d | 0.00d | 0.00c | 0.00b |
| Permethrin | 100.00a | 90.50a | 97.50a | 97.50a | 97.50a | 67.00a |
| Control | 1.75c | 0.00d | 0.00d | 0.00d | 0.00c | 0.00b |

Within a column, mortality means followed by different letters are significantly different ($p<0.05$). Plywood panels (225 $cm^2$) were treated with chemicals at a rate of 1.67 mg $cm^{-2}$. Panels were treated on day 0 and was held until exposure on post-treatment day. Mosquitoes were exposed to chemicals for 2 h, and mortality rate was assessed 24 h after initial exposure. Control contained formulation ingredients without semiochemicals.

EXAMPLE 14

Determination of Toxic Effects of Melafleur, CYCLEMONE A™ and Beta Damascone Formulations Applied on Ply-Wood Panel Boards Against Field-Collected *musca domestica*

To investigate the toxic effects of melafleur, CYCLEMONE A™ and beta damascone formulations applied on ply-wood boards against field-collected house fly, *Musca domestica*, a contact bioassay is performed according to the following procedures.

Briefly, one *Musca domestica* strain and one other *Musca domestica* strain are obtained as is illustrated in Example 3. Each fly strain is divided into seven sets: three sets as the experiment, three sets as the positive control, and one set as the negative control. Flies are assayed on unpainted plywood panel boards that have been previously exposed to natural summer weather conditions for at least 10 days. In the experimental set, melafleur, CYCLEMONE A™ or beta damascone formulation is applied to the panels at a concentration of 3.33 mg/$cm^2$; while the positive control set is treated with geranyl acetone, rosalva or citronellol, and the negative control set is treated with water. The formulation is applied at a uniform rate of 7.5 ml per 225 $cm^2$, sufficient to cover the entire panel without dripping. Subsequently, the treated panel boards are dried for about an hour.

In each set, 20 adult flies are placed onto panel boards. Flies are secured with wooden embroidery hoops, covered with a coarse mesh screen cloth previously sprayed with the respective formulation. After 4 hours, flies are transferred into a clean jar. The mortality rate is measured 24 hours after the transfer, and is determined using the same procedures as are illustrated in Example 2.

The results, as shown in Table 12, demonstrate that melafleur, CYCLEMONE A™ and beta damascone formulations applied on ply-wood panel boards exhibit significant toxic effects against field-collected *Musca domestica*. For both the Alachua strain and the Gilchrist strain, all three formulations result in a high mortality rate of about 95.0% to 100.0%. In comparison, geranyl acetone, citronellol and rosalva formulations exhibit weak or no toxic effects at all.

TABLE 12

Toxic Effects of Melafleur, CYCLEMONE A ™ and Beta Damascone Formulations Applied on Ply-wood Panel Boards against Field-collected *Musca domestica*

| | % mortality | |
|---|---|---|
| Semiochemical | Gilchrist | Alachua |
| Beta damascene | 97.50a | 100.00a |
| Citronellol | 0.00c | 2.25c |
| Cyclemone A | 95.00a | 100.00a |
| Geranyl acetone | 44.50b | 47.50b |
| Melafleur | 100.00a | 100.00a |
| Rosalva | 1.10c | 2.75c |
| Control | 3.75c | 4.25c |

Within a column, mortality means followed by different letters are significantly different ($p<0.05$). Plywood panels (225 $cm^2$) were treated with chemicals at a rate of 1.67 mg $cm^{-2}$. Panels were treated on day 0 and was held until exposure on post-treatment day. Mosquitoes were exposed to chemicals for 2 h, and mortality rate was assessed 24 h after initial exposure. Control contained formulation ingredients without semiochemicals.

EXAMPLE 15

Determination of the Residual Toxicity of Melafleur, CYCLEMONE A™ and Beta Damascone Formulations Applied on Ply-Wood Panel Boards Against *Ae. aegypti*

To investigate the residual toxicity of melafleur, CYCLEMONE A™ and beta damascone formulations applied on ply-wood panel boards against yellow fever mosquitoes, *Ae. aegypti*, a residual contact bioassay is performed according to the following procedures.

Briefly, after mosquitoes are assayed on unpainted plywood panel boards with formulation at a concentration of 1.67 mg $cm^{-2}$ for 2 hours, they are transferred into a separate glass jar, and held for another 24 hours. The mortality rate is measured daily for a continuous 4 days (Day 1 starts at 24 hours after the transfer), as is determined using the same procedures as are illustrated in Example 2. The results, as shown in Table 13, demonstrate that melafleur, CYCLEMONE A™ and beta damascone formulations applied on ply-wood panel boards exhibit significant toxic effects against *Ae. aegypti*. All three formulations result in a high mortality rate of above 96% on Day 1 and above 59% on Day 2. They also exhibit significantly higher toxicity compared to geranyl acetone and rosalva.

TABLE 13

Residual Toxicity of Melafleur, CYCLEMONE A ™ and Beta Damascone Formulations Applied on Ply-wood Panel Boards against *Aedes aegypti*

| Semiochemical | % mortality on various days following treatment | | | |
|---|---|---|---|---|
| | 1 | 2 | 3 | 4 |
| Beta damascene | 96.00a | 59.00b | 19.0bc | 8.50bc |
| Citronellol | 94.00a | 61.0b | 26.0b | 10.0b |
| Cyclemone A | 100.00a | 72.00b | 28.0b | 13.0b |
| Geranyl acetone | 84.00a | 25.0c | 8.0c | 5.0c |
| Melafleur | 100.00a | 68.00b | 34.0b | 19.25b |
| Permethrin | 100.00a | 99.00a | 98.0a | 96.50a |
| Rosalva | 58.00b | 34.0c | 11.0 | 3.25.c |
| Control | 0.000c | 3.00d | 5.0cd | 2.75c |

Within a column, mortality means followed by different letters are significantly different (p<0.05). Plywood panels (225 cm$^2$) were treated with chemicals at a rate of 1.67 mg cm$^{-2}$. Panels were treated on day 0 and was held until exposure on post-treatment day. Mosquitoes were exposed to chemicals for 2 h, and mortality rate was assessed 24 h after initial exposure. Control contained formulation ingredients without semiochemicals.

EXAMPLE 16

Determination of Impact of Melafleur, CYCLEMONE A™ and Beta Damascone on Honey Bee Behaviors To investigate the impact of melafleur, CYCLEMONE A™ and beta damascone on honey bee behaviors, an olfactory response assay is performed using an open-port design in a MEDUSA™ olfactometer.

Briefly, in the experimental set, artificial host membranes treated with 0.25 mg semiochemical are applied to perfumery strips. These perfumery strips are placed in TYGON® tubes attached to olfactometer ports, facing the incoming airstream. In the positive control set, perfumery strips are treated with fresh honey. In the negative control set, perfumery strips are untreated with any compound.

Twenty five female honey bees, *Apis mellifera* obtained from the honeybee colony at the University of Florida are added into the olfactometer chamber. Each contact between the honeybee and the perfumery strip is recorded by the olfactometer, and the data are archived according to the number of contact seconds per hour. Ten replications are conducted, each with a new set of honey bees. Eight sets of 1-hour recording are obtained.

The data are further analyzed under the Tukey's HSD test using the SAS software version 9.1. The Tukey's mean separation test at α=0.05 is applied. Results show that melafleur, CYCLEMONE A™ and beta damascone do not attract or repel honey bees ($F_{7,72}$=0.705, p=0.67) (data not shown).

It should be understood that the examples and embodiments described herein are for illustrative purposes only and that various modifications or changes in light thereof will be suggested to persons skilled in the art and are to be included within the spirit and purview of this application.

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All patents, patent applications, provisional applications, and publications referred to or cited herein are incorporated by reference in their entirety, including all figures and tables, to the extent they are not inconsistent with the explicit teachings of this specification.

We claim:

1. A method for killing an insect, comprising contacting an insect with an insecticidal formulation, wherein the formulation comprises an insecticidally effective amount of a compound selected from the group consisting of:

i) Compound 1:

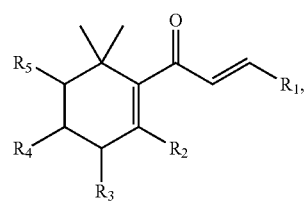

wherein R₁-R₅ is —H or alkyl; and
ii) Compound 2:

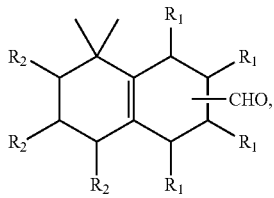

wherein R₁-R₂ is —H or alkyl, and wherein the insect is killed as a result of being contacted with said compound.

2. The method, according to claim 1, wherein the insect is a mosquito or a fly.

3. The method, according to claim 2, wherein the insect is selected from the group consisting of *Aedes aegypti, Aedes albopictus, Anopheles quadrimaculatus, Anopheles earlei, Anopheles punctipennis, Anopheles quadrimaculatus, Anopheles walkeri, Culex pipiens, Culex quinquefasciatus, Culex restuans, Culex salinarius, Ochlerotatus japonicus, Aedes cinereus, Aedes vexans, Ochlertatus abserratus, Ochlertatus atropalpus, Ochlertatus decticus, Ochlertatus implicatus, Ochlertatus intrudens, Ochlertatus sollicitans, Ochlertatus excrucians, Musca domestica, Stomoxys calcitrans, Lutzomyia shannoni, Fannia canicularis, Hydrotaea aenescens, Calliphora* sp., *Phaenicia* spp., and *Musca autumnalis*.

4. The method, according to claim 1, wherein the formulation comprises said compound at a concentration of about 10 μg cm⁻² to 100 μg cm⁻².

5. The method, according to claim 1, wherein the formulation is an aqueous solution, aqueous concentrate, solid concentrate, powder, emulsion, emulsified concentrate, paste, granule, or spray.

6. The method, according to claim 1, wherein the formulation is an aqueous solution.

7. The method, according to claim 1, wherein the formulation is an emulsified concentrate.

8. The method, according to claim 1, wherein the formulation is impregnated or encapsulated in a material.

9. The method, according to claim 1, wherein the formulation comprises an insecticidally effective amount of a compound selected from beta damascone:

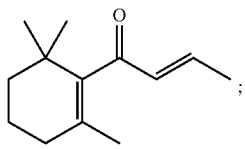

2-naphthaldehyde,1,2,3,4,5,6,7,8-octahydro-8,8-dimethyl:

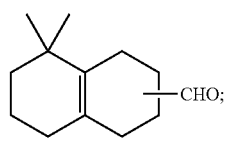

and
5,5-dimethyl-octahydro-2-naphthalene-carboxaldehyde:

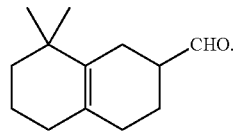

10. The method, according to claim 1, wherein the formulation comprises an insecticidally effective amount of a compound having the structure of Compound 1:

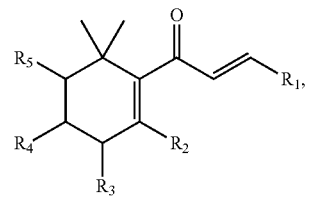

wherein R₁-R₅ is —H or alkyl.

11. The method, according to claim 1, wherein the formulation comprises an insecticidally effective amount of a compound having the structure of Compound 2:

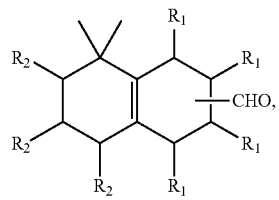

wherein R₁-R₂ is —H or alkyl.

12. The method, according to claim 1, wherein the formulation comprises an insecticidally effective amount of beta damascone:

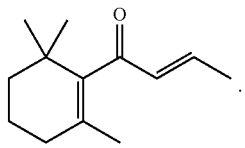

13. The method, according to claim 1, wherein the formulation comprises an insecticidally effective amount of 2-naphthaldehyde,1,2,3,4,5,6,7,8-octahydro-8,8-dimethyl:

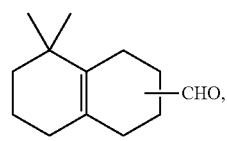

14. The method, according to claim 1, wherein the formulation comprises an insecticidally effective amount of 5,5-dimethyl-octahydro-2-naphthalene-carboxaldehyde:

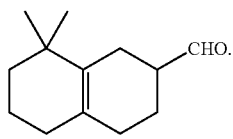

15. The method, according to claim 12, wherein the insect is a mosquito or a fly.

16. The method, according to claim 13, wherein the insect is a mosquito or a fly.

17. The method, according to claim 14, wherein the insect is a mosquito or a fly.

18. The method, according to claim 12, wherein the insect is selected from the group consisting of *Aedes aegypti, Aedes albopictus, Anopheles quadrimaculatus, Anopheles earlei, Anopheles punctipennis, Anopheles quadrimaculatus, Anopheles walkeri, Culex pipiens, Culex quinquefasciatus, Culex restuans, Culex salinarius, Ochlerotatus japonicus, Aedes cinereus, Aedes vexans, Ochlertatus abserratus, Ochlertatus atropalpus, Ochlertatus decticus, Ochlertatus implicatus, Ochlertatus intrudens, Ochlertatus sollicitans, Ochlertatus excrucians, Musca domestica, Stomoxys calcitrans, Lutzomyia shannoni, Fannia canicularis, Hydrotaea aenescens, Calliphora* sp., *Phaenicia* spp., and *Musca autumnalis*.

19. The method, according to claim 13, wherein the insect is selected from the group consisting of *Aedes aegypti, Aedes albopictus, Anopheles quadrimaculatus, Anopheles earlei, Anopheles punctipennis, Anopheles quadrimaculatus, Anopheles walkeri, Culex pipiens, Culex quinquefasciatus, Culex restuans, Culex salinarius, Ochlerotatus japonicus, Aedes cinereus, Aedes vexans, Ochlertatus abserratus, Ochlertatus atropalpus, Ochlertatus decticus, Ochlertatus implicatus, Ochlertatus intrudens, Ochlertatus sollicitans, Ochlertatus excrucians, Musca domestica, Stomoxys calcitrans, Lutzomyia shannoni, Fannia canicularis, Hydrotaea aenescens, Calliphora* sp., *Phaenicia* spp., and *Musca autumnalis*.

20. The method, according to claim 14, wherein the insect is selected from the group consisting of *Aedes aegypti, Aedes albopictus, Anopheles quadrimaculatus, Anopheles earlei, Anopheles punctipennis, Anopheles quadrimaculatus, Anopheles walkeri, Culex pipiens, Culex quinquefasciatus, Culex restuans, Culex salinarius, Ochlerotatus japonicus, Aedes cinereus, Aedes vexans, Ochlertatus abserratus, Ochlertatus atropalpus, Ochlertatus decticus, Ochlertatus implicatus, Ochlertatus intrudens, Ochlertatus sollicitans, Ochlertatus excrucians, Musca domestica, Stomoxys calcitrans, Lutzomyia shannoni, Fannia canicularis, Hydrotaea aenescens, Calliphora* sp., *Phaenicia* spp., and *Musca autumnalis*.

\* \* \* \* \*